US009694021B2

(12) United States Patent
Chowhan et al.

(10) Patent No.: US 9,694,021 B2
(45) Date of Patent: Jul. 4, 2017

(54) PHARMACEUTICAL COMPOSITIONS WITH PHOSPHONIUM ANTIMICROBIAL AGENTS

(71) Applicant: Alcon Research, Ltd., Fort Worth, TX (US)

(72) Inventors: Masood A. Chowhan, Arlington, TX (US); Wesley Wehsin Han, Arlington, TX (US); L. Wayne Schneider, Crowley, TX (US)

(73) Assignee: ALCON RESEARCH, LTD, Fort Worth, TX (US)

( * ) Notice: Subject to any disclaimer, the term of this patent is extended or adjusted under 35 U.S.C. 154(b) by 138 days.

(21) Appl. No.: 14/085,230

(22) Filed: Nov. 20, 2013

(65) Prior Publication Data

US 2014/0080793 A1    Mar. 20, 2014

Related U.S. Application Data (63) Continuation of application No. 13/093,995, filed on Apr. 26, 2011, now abandoned.

(60) Provisional application No. 61/328,815, filed on Apr. 28, 2010.

(51) Int. Cl.
*A61K 31/662* (2006.01)
*A61K 31/66* (2006.01)
(Continued)

(52) U.S. Cl.
CPC ............ *A61K 31/66* (2013.01); *A61K 9/0043* (2013.01); *A61K 9/0046* (2013.01); *A61K 9/0048* (2013.01); *A61K 31/662* (2013.01); *A61K 33/42* (2013.01)

(58) Field of Classification Search
CPC ............................ A61K 31/662; A61K 31/66
USPC ............................................ 514/129, 125, 77
See application file for complete search history.

(56) References Cited

U.S. PATENT DOCUMENTS 3,281,365 A   10/1966   Moedritzer
3,294,632 A   12/1966   Wagner (Continued)

FOREIGN PATENT DOCUMENTS

EP   0979659 A1   2/2000
EP   2563375 A1   3/2013
(Continued)

OTHER PUBLICATIONS

Kanazawa et al, "Synthesis and Antimicrobial Activity of Dimethyl- and Trimethyl-Substituted Phophonium Salts with Alkyl Chains of Various Lengths," Antimicrobial Agents and Chemotherapy (1994), pp. 945-952.*

(Continued)

*Primary Examiner* — Kamal Saeed
*Assistant Examiner* — Janet L Coppins
(74) *Attorney, Agent, or Firm* — Mark Flanigan (57) ABSTRACT

The present invention is related to pharmaceutical compositions that include a phosphonium antimicrobial agent. In a preferred embodiment, the present invention relates to an otic, nasal or ophthalmic composition (e.g., an aqueous ophthalmic solution) that includes a phosphonium salt compound as an antimicrobial agent. The compositions typically possess sufficient antimicrobial activity to satisfy USP preservative efficacy requirements and/or similar preservative standards (e.g., EP and JP).

7 Claims, 2 Drawing Sheets

(51) Int. Cl.
*A61K 33/42* (2006.01)
*A61K 9/00* (2006.01)

(56) References Cited

U.S. PATENT DOCUMENTS

| | | | |
|---|---|---|---|
| 3,998,754 A | 12/1976 | Oswald | |
| 4,188,380 A | 2/1980 | Oswald | |
| 4,673,509 A | 6/1987 | Talbot | |
| 4,874,526 A | 10/1989 | Thomas | |
| 5,102,874 A | 4/1992 | Lehmann | |
| 5,366,727 A * | 11/1994 | Kanazawa et al. | 424/78.35 |
| 5,520,910 A | 5/1996 | Inaba | |
| 6,160,069 A | 12/2000 | Kawai | |
| 6,190,651 B1 | 2/2001 | Matano | |
| 6,579,859 B1 | 6/2003 | Tafel | |
| 6,939,554 B2 | 9/2005 | Huang | |
| 2001/0016190 A1 | 8/2001 | Oono | |
| 2001/0055603 A1 | 12/2001 | Oono | |
| 2011/0269719 A1 | 11/2011 | Chowhan | |

FOREIGN PATENT DOCUMENTS

| | | |
|---|---|---|
| WO | 95/31956 A1 | 11/1995 |
| WO | 95/31996 A1 | 11/1995 |
| WO | 01/87900 A1 | 11/2001 |
| WO | 2011/137090 A1 | 11/2011 |

OTHER PUBLICATIONS

Ciba-Geigy PLC: Biocide, Research Disclosure, Mason Publications, Hampshire, GB, vol. 225, No. 20, Jan. 1, 1983.
Kanazawa et al., 1994, "Synthesis and Antimicrobial Activity of Dimethyl- and Trimethyl-Substituted Phosphonium Salts with Alkyl Chains of Various Lengths", Antimicrobial Agents and Chemotherapy, vol. 38(5), 945-952, May 1994.
PCT International Search Report for corresponding PCT/US2011/033857 with mailing date Jun. 21, 2011.
Cieniecka-Roslonkiewicz, et al., "Synthesis, anti-microbial activities and anti-electrostatic properties of phosphonium-based ionic liquids", Green Chemistry, vol. 7 No. 12, pp. 855-862, Dec. 2005.
Japanese National Phase PCT Laid-open Publication No. 10-500686 (English language member of the same patent family: WO 95/31996).
Japanese National Phase PCT Laid-open Publication No. 10-500687 (English language member of the same patent family: WO 95/31956).
Japanese Laid-Open Publication No. 2003-137712 (No English language counterpart could be located-Abstract attached).

* cited by examiner

PHARMACEUTICAL COMPOSITIONS WITH PHOSPHONIUM ANTIMICROBIAL AGENTS

CROSS REFERENCE TO RELATED APPLICATION

This application is a continuation application of U.S. application Ser. No. 13/093,995, filed Apr. 26, 2011, which claims priority of U.S. Provisional Patent Application Ser. No. 61/328,815, filed Apr. 28, 2010.

TECHNICAL FIELD OF THE INVENTION

The present invention is related to pharmaceutical compositions that include a phosphonium antimicrobial agent. In a preferred embodiment, the present invention relates to an otic, nasal or ophthalmic composition (e.g., an aqueous ophthalmic solution) that includes a phosphonium salt compound as an antimicrobial agent.

BACKGROUND OF THE INVENTION

Pharmaceutical compositions, particularly ophthalmic, otic and nasal compositions, that are utilized multiple times by a patient are often referred to as being of a "multi-dose" nature. Such compositions can be manufactured under sterile conditions via procedures that are well known to those skilled in the art. However, once the packaging for a product is opened, such that the composition contained therein is exposed to the atmosphere and other sources of potential microbial contamination (e.g., the hands of a human patient), the sterility of the product may be compromised. Thus, such pharmaceutical compositions typically require the use of a preservative to aid in the prevention of growth of fungal and bacterial microbes. Moreover, such preservatives are typically required to assure that those compositions comply with preservation efficacy requirements of the United States Pharmacopeia ("USP") and/or analogous guidelines in other countries.

While such preservatives are typically needed to provide required preservation efficacy, those same preservatives can exhibit variable degrees of discomfort and/or toxicity to bodily tissue. Moreover, multi-dose pharmaceutical compositions are often designed to repeatedly come in to contact with particular portions of the body (e.g., the cornea of the eye or other bodily tissue), either directly or indirectly, and those body portions can be particularly sensitive to exogenous chemical agents. Consequently, in order to minimize the potential for harmful effects to such tissue, it is preferable to use anti-microbial preservatives that are relatively non-toxic to that tissue, and to use such preservatives at relatively low concentrations.

A desired balance between anti-microbial efficacy and potential toxicological effects of anti-microbial preservatives is often difficult to achieve. More specifically, the concentration of an antimicrobial agent necessary for the preservation of multi-dose pharmaceutical formulations from microbial contamination may create the potential for toxicological effects on the cornea and/or other bodily tissues. Using lower concentrations of the anti-microbial agents generally helps to reduce the potential for such toxicological effects, but the lower concentrations may be insufficient to achieve the required level of biocidal efficacy (i.e., antimicrobial preservation).

In view of this balance, the pharmaceutical industry continues to seek antimicrobial agents that provide a high degree of preservation efficacy while exhibiting a relatively low degree of toxicity.

SUMMARY OF THE INVENTION

Accordingly, the present invention is directed to a pharmaceutical composition, preferably an ophthalmic pharmaceutical composition, comprising:
an phosphonium antimicrobial agent according to the following formula:

wherein:
$R_1$, $R_2$, $R_3$ and $R_4$ are independently selected from the group consisting of H, alkyl (e.g., methyl or ethyl), aryl (e.g., phenyl), alkoxy, hydroxyl, hydroxyalkyl or alcohol; and
$X^-$ is a counterion; and
water;
wherein the phosphonium antimicrobial agent is at least 0.0001 w/w % of the composition and is no greater than 0.5 w/w %; and
wherein the composition is suitable for parenteral, oral or topical administration to a human being; and
wherein either:
i. at least two of $R_1$, $R_2$, $R_3$ and $R_4$ are a hydroxyalkyl group; or
ii. at least one of $R_1$, $R_2$, $R_3$ and $R_4$ is a long alkyl chain of at least 8 carbons; or
iii. both.

DETAILED DESCRIPTION OF THE INVENTION

The present invention is predicated upon the provision of a pharmaceutical composition that includes a phosphonium compound as an antimicrobial agent. Advantageously, it has been found that such compositions can be formulated to exhibit relatively high degrees of anti-microbial activity while also exhibiting relatively low toxicity. Such phosphonium compounds have been found to be particularly useful as antimicrobial agents in ophthalmic compositions such as contact lens disinfecting solutions and ophthalmic pharmaceutical compositions (i.e., ophthalmic compositions includes an ophthalmic therapeutic agent).

Compositions of the present invention include a phosphonium compound having the following formula:

wherein:

R₁, R₂, R₃ and R₄ are independently selected from the group consisting of H, alkyl (e.g., methyl or ethyl), aryl (e.g., phenyl), alkoxy, hydroxyl, hydroxyalkyl, alcohol, and

X⁻ is an anionic counterion.

The counterion X⁻ can be selected from a sulfate, a sulfonate, a borate, a phosphate, a halogen, a halogen containing compound, an inorganic acid, citrate, acetate or other organic acid, any combinations thereof or the like. Preferably the counterion X⁻ is a halogen or halogen containing compound such as chloride, bromide, fluoride, iodide, tertafluoroborate, combinations thereof or the like.

Examples of suitable phosphonium antimicrobial agents include, without limitation, Tetrakis(hydroxymethyl)phosphonium chloride, Tributyl-tetradecylphosphonium chloride, Tributyldodecylphosphonium bromide, Tributylhexadecylphosphonium bromide, Triphenyltetradecylphosphonium bromide, Triphenyldodecylphosphomium bromide, Trihexyltetradecylphosphonium, Trihexyltetradecylphosphonium chloride, Benzyldimethyldodecylphosphonium chloride, Benzyldimethyltetradecylphosphonium chloride, Benzyldihydroxymethyldodecylphosphonium chloride, Benzyldihydroxymethyltetradecylphosphonium chloride, Trihydroxymethyldodecylphosphonium chloride, and Trihydroxymethyltetradecylphosphonium chloride, or any combinations thereof. The antimicrobial agent may be selected from any of these compounds or any combinations thereof.

It has been found that R₁, R₂, R₃ and R₄ groups of the phosphonium antimicrobial agents of the present invention can have significant effects on the characteristics of those agents. Generally, the compounds having one or two of the R₁, R₂, R₃ and R₄ groups as relatively long aliphatic chains (i.e., chains of at least 8 or 9, more typically at least 10 and even possibly at least 12 or 14 carbons, but also typically no greater than 20, more typically no greater than 16, and even possibly no greater than 14 or even 12 carbons) exhibit relatively high degrees of antimicrobial efficacy where the remainder of those groups (two or three of groups) are smaller organic, inorganic or alkyl groups (e.g., branched, unbranched or cyclic alkyl groups) with no greater than 7, more typically no greater than 6 and even possibly no greater than 4 carbons. These molecules also tended to exhibit relatively low cytotoxicity relative to other antimicrobial compounds (e.g., benzalkonium chloride), which are presently widely used in ophthalmic and other pharmaceutical products. This is believed to be particularly the case when these phosphonium compounds are used on a equimolar basis relative to other antimicrobials.

It is believed that the following compound is likely to be particularly desirable phosphonium antimicrobial agents:

BenzylDimethylAlkylPhosphonium Chloride
Alkyl Chain Lengths from C10 or C12 to C16

Relative to the above compounds, it has also been observed that compounds having very similar or same R₁, R₂, R₃ and R₄ groups, particularly same or similar alkyl groups, tend to exhibit less desirable antimicrobial efficacy. Most advantageously, however, one particular group of phosphonium compounds has been identified as being anomalous relative to this observation. This groups of compounds having multiple R₁, R₂, R₃ and R₄ groups that are similar or the same has be shown to provide highly desirable preservation efficacy while providing very low degrees of toxicity. For these compounds, two, and more preferably three or all of the R₁, R₂, R₃ and R₄ groups are a hydroxyalkyl group or a hydroxyl groups. Thus, in a preferred embodiment, at least two, more typically at least two, even more typically at least three and even more typically all of R₁, R₂, R₃ and R₄ are independently selected from the group consisting of hydroxyl and hydroxyalkyl. In a preferred embodiment, at least one, more typically at least two, even more typically at least three and even more typically all of R₁, R₂, R₃ and R₄ are hydroxyalkyl (e.g., hydroxymethyl). Moreover, when two or more of the R₁, R₂, R₃ and R₄ groups are hydroxyalkyl, it is preferred that that the alkyl portions of those groups are the same or differ by no more than two and more preferably no more than one carbon. In a highly preferred embodiment, the hydroxyalkyl groups are selected from the group including hydroxylmethyl, hydroxyethyl and hydroxypropyl groups. It is also preferably for at least two, three or all of R₁, R₂, R₃ and R₄ to be the same group, particularly hydroxymethyl. One particularly preferred phosphonium anti-microbial agent is tetrakishydroxymethyl phosphonium salt, particularly tetrakishydroxymethyl phosphonium chloride.

As an added advantage, the phosphonium antimicrobial agents having hydroxyl group[s], hydroxyalkyl (e.g., hydroxymethyl) group[s] or a combination thereof for one, two, three or all of R₁, R₂, R₃ and R₄ tend to be relatively hydrophilic and soluble in water. Such compounds can be more easily integrated into ophthalmic compositions as well as other pharmaceutical compositions, particularly aqueous compositions. In preferred embodiments, the phosphonium antimicrobial agent of the present application exhibits a relatively high degree of solubility in water. Such antimicrobial agents can have, for example, a solubility in water that is at least 1.0%, more typically at least 3% and even possibly 10% or 50% at 23° C.

The phosphonium antimicrobial agent can typically be employed at relatively low concentrations within the compositions of the present invention. The phosphonium antimicrobial agent is typically at least about 0.0001 w/w %, more typically at least bout 0.001 w/w %, still more typically at least about 0.005 w/w % of the overall composition. The phosphonium antimicrobial agent is typically no greater than about 0.5 w/w %, more typically no greater than about 0.1 w/w %, still more typically not greater than about 0.05 w/w % and even possibly no greater than about 0.02 or even about 0.008 w/w % of the overall composition.

It is also believed that phosphonium compounds of the present invention having one or two of the R₁, R₂, R₃ and R₄ groups as a long aliphatic chain as described above and having two or three of the R₁, R₂, R₃ and R₄ groups as a hydroxyl, hydroxyalkyl such as hydroxylmethyl or any combination as described above can have desirable antimicrobial and toxicity characteristics. As examples, the following compounds are likely to be particularly desirable phosphonium antimicrobial agents:

Trihydroxymethyl Alkyl Phosphonium Chloride

Benzyl Dihydroxymethyl Alkyl Phosphonium Chloride

It is contemplated that the phosphonium antimicrobial agent of the present invention may be selected from any of the phosphonium antimicrobial agents discussed herein or any combination of the phosphonium antimicrobial agents discussed herein.

Generally it is contemplated that the compositions of the present invention can be configured for parenteral, oral, or topical administration to a mammal, particularly a human being. Preferably, the compositions are configured for ocular, otic or nasal administrations. In a highly preferred embodiment, the compositions are configured for ocular administration by topical administration.

The compositions of the present invention may be provided as creams, gels, suspensions, solutions or the like. Preferably, and particularly for ocular, otic or nasal applications, the compositions of the present invention are aqueous and include a substantial amount of water (e.g., at least 30 w/w %, more typically at least 70 w/w % and even more typically at least 90 or even 96 w/w % water).

It is contemplated that the phosphonium antimicrobial agent of the present application can be used in combination with other preservatives such as benzalkonium chloride (BAK), polymeric quaternary ammonium compound, polyhexamethyl biguanide (PHMB), or the like. However, it has advantageously been found that the phosphonium antimicrobial agent of the present application can be the sole or only preservative within the compositions of the present invention.

The phosphonium antimicrobial compounds of the present invention are particularly useful in aqueous ophthalmic compositions and particularly multi-dose ophthalmic compositions. The term ophthalmic compositions typically encompasses several different types of compositions and the phosphonium compounds of the present invention are useful for the great majority of those compositions. However, the phosphonium compounds of the present invention are particularly useful for therapeutic pharmaceutical ophthalmic compositions and contact lens cleaning and/or disinfecting compositions. For purposes of the present invention, therapeutic pharmaceutical ophthalmic compositions are those compositions that include one or more therapeutic agents for treating an ocular condition while contact lens cleaning and disinfecting compositions are typically without such therapeutic agents. Rather, contact lens cleaning and disinfecting compositions will typically include one or more cleaning agents that remove protein from contact lenses as the lenses soak in the composition.

Non-limiting examples of potential ophthalmic therapeutic agents for the present invention include: anti-glaucoma agents, anti-angiogenesis agents; anti-infective agents; anti-inflammatory agents; growth factors; immunosuppressant agents; and anti-allergic agents. Anti-glaucoma agents include beta-blockers, such as betaxolol and levobetaxolol; carbonic anhydrase inhibitors, such as brinzolamide and dorzolamide; prostaglandins, such as travoprost, bimatoprost, and latanoprost; seretonergics; muscarinics; dopaminergic agonists. Anti-angiogenesis agents include anecortave acetate (RETAANE™, Alcon™ Laboratories, Inc. of Fort Worth, Tex.) and receptor tyrosine kinase inhibitors (RTKi). Anti-inflammatory agents include non-steroidal and steroidal anti-inflammatory agents, such as triamcinolone actinide, suprofen, diclofenac, ketorolac, nepafenac, rimexolone, and tetrahydrocortisol. Growth factors include EGF or VEGF. Anti-allergic agents include olopatadine and epinastine. The ophthalmic drug may be present in the form of a pharmaceutically acceptable salt.

Ophthalmic compositions according to the present invention can also include surfactants, buffering agents, tonicity agents, anti-oxidants, viscosity-modifying agents any combinations thereof or the like.

The composition of the present invention can also include borate, polyol or both for buffering purposes and/or for enhancement of anti-microbial activity. As used herein, the term "borate" shall refer to boric acid, salts of boric acid, borate derivatives and other pharmaceutically acceptable borates, or combinations thereof. Most suitable are: boric acid, sodium borate, potassium borate, calcium borate, magnesium borate, manganese borate, and other such borate salts. As used herein, the term "polyol" includes any compound having at least one hydroxyl group on each of two adjacent carbon atoms that are not in trans configuration relative to each other. The polyols can be linear or cyclic, substituted or unsubstituted, or mixtures thereof, so long as the resultant complex is water soluble and pharmaceutically acceptable. Examples of such compounds include: sugars, sugar alcohols, sugar acids and uronic acids. Preferred polyols are sugars, sugar alcohols and sugar acids, including, but not limited to: mannitol, glycerin, xylitol, sorbitol and propylene glycol. Mannitol is a particularly preferred polyol as is illustrated in the examples included herein. As such, in a preferred embodiment, the polyol of the composition is entirely or substantially entirely (i.e., at least 70% by weight) mannitol.

As is known, borate interacts with polyols, such as glycerol, propylene glycol, sorbitol and mannitol, to form borate polyol complexes. The type and ratio of such complexes depends on the number of OH groups of a polyol on adjacent carbon atoms that are not in trans configuration relative to each other. It shall be understood that weight/volume percentages of the ingredients polyol and borate include those amounts whether as part of a complex or not.

Polyol is typically at least 0.005 w/v %, more typically at least 0.05 w/v % and even possibly at least 0.1 w/v % of the composition. Polyol is typically no greater than 2.0 w/v %, more typically no greater than 1.0 w/v % and even possibly no greater than 0.2 w/v % of the composition. In a preferred embodiment, the polyol includes or is entirely or substantially entirely mannitol and the amount of mannitol is at least 0.03 w/v %, more typically at least 0.07 w/v % and even possibly at least 0.09 w/v % of the composition and is typically no greater than 1.5 w/v %, more typically no greater than 1.0 w/v % and even possibly no greater than 0.13 w/v % of the composition.

Borate, particularly when the borate is entirely or substantially entirely boric acid, is typically at least 0.05 w/v %, more typically at least 0.18 w/v % and even possibly at least 0.27 w/v % of the composition and is typically no greater than 1.0 w/v %, more typically no greater than 0.5 w/v %, still more typically no greater than 0.4 w/v % and even possibly no greater than 0.35 w/v % or 0.33 w/v % of the composition.

Ophthalmic compositions are typically provided in dispensers. These dispensers typically contain at least 0.5 ml, more typically at least 3 ml and more typically at least 10 ml of the composition but contains no greater than 50,000 ml, more typically no greater than 10,000 ml, more typically no greater than 1000 ml of the composition. Therapeutic pharmaceutical ophthalmic compositions are preferably provided in a dispenser such as an eye dropper and these eye dropper typically contain at least 0.5 ml, more typically at least 1.0 ml and even more typically at least 2.0 ml of the pharmaceutical composition and typically contain no greater than about 100 ml, more typically no greater than about 50 ml and even more typically no greater than 20 ml of the pharmaceutical composition. Contact lens cleaning and/or disinfecting compositions are preferably provided in a dispenser that contains at least 10 ml, more typically at least 30 ml and even more typically at least 70 ml of the composition and typically contain no greater than about 10,000 ml, more typically no greater than about 1000 ml and even more typically no greater than 300 ml of the composition.

It is also contemplated that the compositions of the present invention may include or be used in conjunction with one or more oxidizing agents. Such oxidizing agents might be particularly desirable for use with contact lens cleaning and/or disinfecting solutions. The oxidizing agent[s] may be included as part of a single solution or may be provided as part of a two part system. Oxidizing agents suitable for use in the compositions of the present invention include, without limitation, peroxides (e.g., hydrogen peroxide, urea peroxide or the like); peroxide generating compounds such as perborates (e.g., sodium perborate) and peracetic acid; sodium chlorite and chlorine dixide, any combinations thereof or the like.

When the oxidizing agent is used as part of a two part system, the oxidizing agent is typically provided the main antimicrobial agent in a solution. In such circumstances, the phosphonium antimicrobial agent is provided as a back-up antimicrobial to prevent regrowth of microbes. Of course, the phosphonium antimicrobial agent may be provided as the main anti-microbial agent in such a system as well.

When the oxidizing agent is part of a single solution, it is typically used at a relatively low concentration. Typically the oxidizing agent will be at least 0.00001 w/w %, more typically at least 0.0001 w/w % and possibly at least 0.0005 w/w % of the composition. The oxidizing agent will typically be no greater than 0.01 w/w %, more typically no greater than 0.001 w/w % and even more typically no greater than 0.0007 w/w % of the composition.

The present invention is particularly useful for the provision of multi-dose pharmaceutical (e.g., ophthalmic) compositions that have sufficient antimicrobial activity to allow the compositions to satisfy the USP preservative efficacy requirements, as well as other preservative efficacy standards for aqueous pharmaceutical compositions.

The preservative efficacy standards for multi-dose ophthalmic solutions in the U.S. and other countries/regions are set forth in the following table:

| Preservative Efficacy Test ("PET") Criteria (Log Order Reduction of Microbial Inoculum Over Time | | |
|---|---|---|
| | Bacteria | Fungi |
| USP 31 | A reduction of 1 log (90%), by day 7; 3 logs (99.9%) by day 14; and no increase after day 14 | The compositions must demonstrate over the entire test period, which means no increases of 0.5 logs or greater, relative to the initial inoculum. |
| Japan | 3 logs by 14 days; and no increase from day 14 through day 28. | No increase from initial count at 14 and 28 days |
| Ph. Eur. A[1] | A reduction of 2 logs (99%) by 6 hours; 3 logs by 24 hours; and no recovery after 28 days | A reduction of 2 logs (99%) by 7 days, and no increase thereafter |
| Ph. Eur. B | A reduction of 1 log at 24 hours; 3 logs by day 7; and no increase thereafter | A reduction of 1 log (90%) by day 14, and no increase thereafter |

[1]There are two preservative efficacy standards in the European Pharmacopoeia "'A" and "B".

The standards identified above for the USP 31 are substantially identical to the requirements set forth in prior editions of the USP.

The compositions of the present invention are often formulated as sterile aqueous solutions. The ophthalmic compositions of the present invention are also formulated so as to be compatible with the eye and/or other tissues to be treated with the compositions. The ophthalmic compositions intended for direct application to the eye will be formulated so as to have a pH and tonicity that are compatible with the eye. It is also contemplated that the compositions can be suspensions or other types of solutions.

The compositions will typically have a pH in the range of 4 to 9, preferably 5.5 to 8.5, and most preferably 5.5 to 8.0. Particularly desired pH ranges are 6.0 to 8.0 and more specifically 6.4 to 7.8. The compositions will typically have an osmolality that is at least 200 milliosmoles per kilogram (mOsm/kg), more typically at least 240 mOsm/kg and even more typically at least 260 mOsm/kg. The compositions will typically have an osmolality that is no greater than 380 mOsm/kg, more typically no greater than 360 mOsm/kg and even more typically no greater than 330 mOsm/kg.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

Table A below provides a listing of exemplary ingredients suitable for an exemplary preferred formulations of the composition, particularly ophthalmic composition, of the present invention and a desired weight/volume percentage for those ingredients.

TABLE A

| Ingredient | Formula I w/v percent | Formula II w/v percent | Formula III w/v percent | Formula IV w/v percent |
|---|---|---|---|---|
| Therapeutic Agent | 0.5 | 0.5 | 0.5 | 0.5 |
| Phosphonium Antimicrobial Agent | 0.005 | 0.003 | 0.003 | 0.02 |
| Carbopol 974P | 0.4 | 0.45 | | |
| Tyloxapol | 0.05 | 0.025 | | |
| Boric Acid | | 0.3 | | |
| Dibasic Sodium Phosphate | | | 0.14 | 0.14 |
| Mannitol | 3.3 | 0.3 | | |
| Sodium Chloride | 0.25 | 0.28 | 0.8 | 0.8 |
| Propylene Glycol | | 0.75 | | |
| NaOH/HCl q.s. to pH | pH = 7.4 | pH = 7.4 | pH = 7.4 | pH = 7.4 |
| purified water q.s. | q.s. to 100 | q.s. to 100 | q.s. to 100 | q.s. to 100 |

It is understood that the weight/volume percents in table A can be varied by ±10%, ±20%, ±30%, ±90% of those weight/volume percents or more and that those variances can be specifically used to create ranges for the ingredients of the present invention. For example, an ingredient weight/volume percent of 10% with a variance of ±20% means that the ingredient can have a weight/volume percentage range of 8 to 12 w/v %.

Table B below provides a listing of exemplary ingredients suitable for an exemplary preferred formulations of the composition, particularly ophthalmic composition, of the present invention and a desired weight/volume percentage for those ingredients.

TABLE B

| Ingredient | w/v percent | w/v percent | w/v percent | w/v percent |
|---|---|---|---|---|
| Phosphonium Antimicrobial Agent | 0.005 | 0.003 | 0.003 | 0.02 |
| Tetronic 1304 | 0.05 | 0.025 | | |
| Boric Acid | | 0.3 | | |
| Dibasic Sodium Phosphate | | | 0.14 | 0.14 |
| Mannitol | 3.3 | 0.3 | | |
| Sodium Chloride | 0.25 | 0.28 | 0.8 | 0.8 |
| Propylene Glycol | | 0.75 | | |
| NaOH/HCl q.s. to pH | pH = 7.4 | pH = 7.4 | pH = 7.4 | pH = 7.4 |
| purified water q.s. | q.s. to 100 | q.s. to 100 | q.s. to 100 | q.s. to 100 |

It is understood that the weight/volume percents in table A can be varied by ±10%, ±20%, ±30%, ±90% of those weight/volume percents or more and that those variances can be specifically used to create ranges for the ingredients of the present invention. For example, an ingredient weight/volume percent of 10% with a variance of ±20% means that the ingredient can have a weight/volume percentage range of 8 to 12 w/v %.

It should also be understood that the formulations of Table B are most suitable as contact lens cleaning and disinfecting solutions and might also be used in conjunction with an oxidizing agent as described above.

The following examples are presented to further illustrate selected embodiments of the present invention. The formulations shown in the examples were prepared using procedures that are well-known to persons of ordinary skill in the field of ophthalmic pharmaceutical compositions.

Examples

Concentrations for the various ingredients of the compositions of the examples provided below are w/v % unless otherwise specifically stated. The compositions of Examples A-D and their preservation efficacy testing (PET) results are provided below.

| Composition | A | B | C | D |
|---|---|---|---|---|
| Phosphonium Compound Name | C12/C14 BAC Control | Dodecyl Tributyl Phosphonium Bromide | Tetradecyl Tributyl Phosphonium Chloride | Hexadecyl Tributyl Phosphonium Bromide |
| Phosphonium Cpd Conc. | 0.01% | 0.013 | 0.0124% | 0.014 |
| Dibasic Sodium Phosphate | 0.14 | 0.14 | 0.14 | 0.14 |
| Sodium Chloride | 0.8 | 0.85 | 0.8 | 0.85 |
| NaOH/HCl | pH 7.4 | pH 7.4 | pH 7.4 | pH 7.4 |
| Purified Water | 100% | 100% | 100% | 100% |
| Staph Aureus (6 Hr/24 Hr/7 Day) | 5.2/5.2/5.2 | 4.9/4.9/4.9 | 5.0/5.0/5.0 | 4.9/4.9/4.9 |
| Pseudomonas A. (6 Hr/24 Hr/7 Day) | 5.0/5.0/5.0 | 2.5/5.0/5.0 | 3.9/4.8/4.8 | 5.0/5.0/5.0 |
| E. Coli (6 Hr/24 Hr/7 Day) | 5.1/5.1/5.1 | 5.0/5.0/5.0 | 4.8/4.8/4.8 | 4.8/4.8/4.8 |
| Candida A. (7 Day) | 5.1 | 4.7 | 4.7 | 4.6 |
| Aspergillus N. (7 Day) | 5.1 | 5.0 | 5.2 | 5.1 |
| PET Results (Pass/Fail) | Pass EP-A | Pass EP-A | Pass EP-A | Pass EP-A |

Composition A is a control composition that shows the preservation efficacy of a solution preserved with benzalkonium chloride. Compositions B through D, however, illustrate the preservation efficacy of solutions substantially identical to those of composition A, but preserved with a phosphonium antimicrobial agent according to an aspect of the present invention. In particular, compositions B-D are preserved with an equimolar amount of a phosphonium antimicrobial agent relative to the benzalkonium chloride in composition A and the phosphonium antimicrobial agent includes a single long chain alkyl group extending from the phosphorous atom. As can be seen, compositions B through D provide similar preservation relative to composition A.

The compositions of Examples E-G and their PET results are provided below.

| Composition | E | F | G |
|---|---|---|---|
| Phosphonium Compound Name | Tetrakis Hydroxymethyl Phosphonium Chloride | Hydroxyethyl Triphenyl Phosphonium Chloride | Tetrabutyl Phosphonium Chloride |
| Phosphonium Cpd Conc. | 0.0054 | 0.0098 | 0.0084 |
| Dibasic Sodium Phosphate | 0.14 | 0.14 | 0.14 |
| Sodium Chloride | 0.85 | 0.85 | 0.85 |
| NaOH/HCl | pH 7.4 | pH 7.4 | pH 7.4 |
| Purified Water | 100% | 100% | 100% |
| Staph Aureus (6 Hr/24 Hr/7 Day) | 4.9/4.9/4.9 | 0.1/0.0/0.3 | 0.0/0.0/0.2 |
| Pseudomonas A. (6 Hr/24 Hr/7 Day) | 5.0/5.0/5.0 | 0.1/0.5/0.1 | 0.0/0.0/0.0 |
| E. Coli (6 Hr/24 Hr/7 Day) | 4.8/4.8/4.8 | 0.0/0.0/0.0 | 0.0/0.0/0.0 |
| Candida A. (7 Day) | 0.1 | 0.1 | 0.0 |
| Aspergillus N. (7 Day) | 0.5 | 0.1 | 0.7 |
| PET Results (Pass/Fail) | Pass USP | Fail All | Fail All |

As can be seen, phosphonium antimicrobial compound E, which has multiple hydroxyalkyl groups (e.g., hydroxymethyl groups) showed significantly superior preservation efficacy relative to phosphonium compounds F and G, which have substantially symmetrical structures like compound E but do not have multiple hydroxyalkyl groups.

The compositions of Examples H-P and their PET results are provided below.

| Composition | H | I | J | K |
|---|---|---|---|---|
| Phosphonium Compound Name | Phenyl Trimethyl Phosphonium Iodide | Diphenyl Dimethyl Phosphonium Iodide | Triphenyl Methyl Phosphonium Chloride | Tetraphenyl Phosphonium Chloride |
| Phosphonium Cpd Conc. | 0.0079 | 0.0098 | 0.0089 | 0.011 |
| Dibasic Sodium Phosphate | 0.14 | 0.14 | 0.14 | 0.14 |
| Sodium Chloride | 0.85 | 0.85 | 0.85 | 0.85 |
| NaOH/HCl | pH 7.4 | pH 7.4 | pH 7.4 | pH 7.4 |
| Purified Water | 100% | 100% | 100% | 100% |
| Staph Aureus (6 Hr/24 Hr/7 Day) | 0.0/0.0/0.1 | 0.0/0.0/0.2 | 0.0/0.0/0.2 | 0.3/0.5/1.9 |
| Pseudomonas A. (6 Hr/24 Hr/7 Day) | 0.1/0.0/0.0 | 0.1/0.0/0.0 | 0.3/0.5/0.0 | 0.2/0.2/0.0 |
| E. Coli (6 Hr/24 Hr/7 Day) | 0.0/0.0/0.0 | 0.1/0.2/0.3 | 0.0/0.0/0.0 | 0.0/0.0/0.1 |
| Candida A. (7 Day) | 0.0 | 0.0 | 0.0 | 0.0 |
| Aspergillus N. (7 Day) | 0.4 | 0.3 | 0.5 | 0.4 |
| PET Results (Pass/Fail) | Fail All | Fail All | Fail All | Fail All |

| Composition | L | M | N |
|---|---|---|---|
| Phosphonium Compound Name | Ethyl Triphenyl Phosphonium Chloride | Butyl Triphenyl Phosphonium Chloride | Nonyl Triphenyl Phosphonium Bromide |
| Phosphonium Cpd Conc. | 0.0093 | 0.01 | 0.013 |
| Dibasic Sodium Phosphate | 0.14 | 0.14 | 0.14 |
| Sodium Chloride | 0.85 | 0.85 | 0.85 |
| NaOH/HCl | pH 7.4 | pH 7.4 | pH 7.4 |
| Purified Water | 100% | 100% | 100% |
| Staph Aureus (6 Hr/24 Hr/7 Day) | 0.0/0.0/0.7 | 0.0/0.0/0.4 | 3.9/5.0/5.0 |
| Pseudomonas A. (6 Hr/24 Hr/7 Day) | 0.3/0.2/0.1 | 0.1/0.0/0.0 | 1.9/2.4/1.1 |
| E. Coli (6 Hr/24 Hr/7 Day) | 0.0/0.0/0.2 | 0.0/0.0/0.0 | 0.2/0.6/2.3 |
| Candida A. (7 Day) | 0.1 | 0.0 | 4.1 |
| Aspergillus N. (7 Day) | 0.1 | 0.1 | 0.9 |
| PET Results (Pass/Fail) | Fail All | Fail All | Fail All |

| Composition | O | P |
|---|---|---|
| Phosphonium Compound Name | Dodecyl Triphenyl Phosphonium Bromide | Tetradecyl Triphenyl Phosphonium Bromide |
| Phosphonium Cpd Conc. | 0.015 | 0.015 |
| Dibasic Sodium Phosphate | 0.14 | 0.14 |
| Sodium Chloride | 0.85 | 0.85 |
| NaOH/HCl | pH 7.4 | pH 7.4 |
| Purified Water | 100% | 100% |
| Staph Aureus (6 Hr/24 Hr/7 Day) | 5.0/5.0/5.0 | 5.0/5.0/5.0 |
| Pseudomonas A. (6 Hr/24 Hr/7 Day) | 4.9/4.9/4.9 | 4.9/4.9/4.9 |
| E. Coli (6 Hr/24 Hr/7 Day) | 4.9/4.9/4.9 | 4.9/4.9/4.9 |
| Candida A. (7 Day) | 4.8 | 4.8 |
| Aspergillus N. (7 Day) | 3.5 | 3.8 |
| PET Results (Pass/Fail) | Pass EP-A | Pass EP-A |

Compositions H-P show that phosphonium antimicrobial agents that include a single long chain alkyl group in accordance with as aspect of the present invention have superior PET results relative to substantially identical compounds that lack the single long chain alkyl group or have an alkyl chain that is too short.

The compositions of Examples Q through T and their PET results are provided below.

| Composition | Q | R | S | T |
|---|---|---|---|---|
| 0.003% Phosphonium Compound | Tetradecyl Tributyl Phosphonium Cl | Hexadecyl Tributyl Phosphonium Br | Tetradecyl Triphenyl Phosphonium Br | Tetrakis Hydroxymethyl Phosphonium Cl |
| Carbopol 974P | 0.45 | 0.45 | 0.45 | 0.45 |
| Tyloxapol | 0.025 | 0.025 | 0.025 | 0.025 |
| Boric Acid | 0.3 | 0.3 | 0.3 | 0.3 |
| Mannitol | 0.3 | 0.3 | 0.3 | 0.3 |
| Sodium Chloride | 0.28 | 0.28 | 0.28 | 0.28 |
| Propylene Glycol | 0.75 | 0.75 | 0.75 | 0.75 |
| NaOH/HCl | pH 7.2 | pH 7.2 | pH 7.2 | pH 7.2 |
| S.A. (6 Hr/24 Hr 7 D/ 14 D/28 D) | 5.1/5.1/ 5.1/5.1/5.1 | 5.1/5.1/ 5.1/5.1/5.1 | 5.1/5.1/ 5.1/5.1/5.1 | 5.1/5.1/ 5.1/5.1/5.1 |
| P.A. (6 Hr/24 Hr 7 D/ 14 D/28 D) | 5.0/5.0/ 5.0/5.0/5.0 | 3.0/5.0/ 5.0/5.0/5.0 | 5.0/5.0/ 5.0/5.0/5.0 | 5.0/5.0/ 5.0/5.0/5.0 |
| E.C. (6 Hr/24 Hr 7 D/ 14 D/28 D) | 5.1/5.1/ 5.1/5.1/5.1 | 2.5/5.1/ 5.1/5.1/5.1 | 5.1/5.1/ 5.1/5.1/5.1 | 4.9/5.1/ 5.1/5.1/5.1 |

-continued

| Composition | Q | R | S | T |
|---|---|---|---|---|
| C.A. (7 D/14 D/28 D) | 4.8/4.8/4.8 | 4.8/4.8/4.8 | 4.8/4.8/4.8 | 0.4/1.2/2.7 |
| A.N. (7 D/14 D/28 D) | 5.0/5.0/5.0 | 5.0/5.0/5.0 | 5.0/5.0/5.0 | 3.9/3.1/2.1 |
| PET Result | Passed EP-A | Passed EP-A | Passed EP-A | Passed USP |

Compositions Q through T illustrate that the phosphonium antimicrobial agent of the present invention provide desirable levels of preservation efficacy in vehicles that include a polymer (e.g., a carboxyvinyl polymer) and/or a surfactant (e.g., tyloxapol), which are ingredients that are particularly desirable for ophthalmic compositions.
The compositions of Examples H-P and their PET results are provided below.

| COMPONENT | % w/v | % w/v | % w/v |
|---|---|---|---|
| Tetrakis-Hydroxymethyl-Phosphonium Chloride | 0.0025 | 0.005 | 0.01 |
| Boric Acid | 0.6 | 0.6 | 0.6 |
| Mannitol | 0.3 | 0.3 | 0.3 |
| Sodium Chloride | 0.5 | 0.5 | 0.5 |
| NaOH/HCl | pH 6.0 | pH 6.0 | pH 6.0 |
| Staph Aureus (6 Hr/24 Hr/7 Day/ 14 Day/28 Day) | 5.0/5.0/ 5.0/5.0/5.0 | 5.0/5.0/ 5.0/5.0/5.0 | 5.0/5.0/ 5.0/5.0/5.0 |
| Pseudomonas A. (6 Hr/24 Hr/7 Day/ 14 Day/28 Day) | 3.3/5.0/ 5.0/5.0/5.0 | 5.0/5.0/ 5.0/5.0/5.0 | 5.0/5.0/ 5.0/5.0/5.0 |
| E. Coli (6 Hr/24 Hr/7 Day/ 14 Day/28 Day) | 5.1/5.1/ 5.1/5.1/5.1 | 5.1/5.1/ 5.1/5.1/5.1 | 5.1/5.1/ 5.1/5.1/5.1 |
| Candida A. (7 Day/14 Day/28 Day) | 0.0/0.2/1.2 | 0.1/0.7/2.0 | 0.9/2.2/3.9 |
| Aspergillus N. (7 D/14 D/28 D) | 3.1/2.9/2.4 | 3.3/3.2/3.2 | 3.2/5.3/5.3 |
| PET Results (Pass/Fail) | Pass USP | Pass USP | Pass EP-B |

Compositions H-P illustrate the enhanced efficacy of phosphonium antimicrobial compounds having multiple hydroxyalkyl groups (e.g., hydroxymethyl groups) when the concentration of those compounds is raised. As will be seen through the discussion below, such concentrations can be raised without necessarily raising the toxicity of the compositions.

Figure 1:
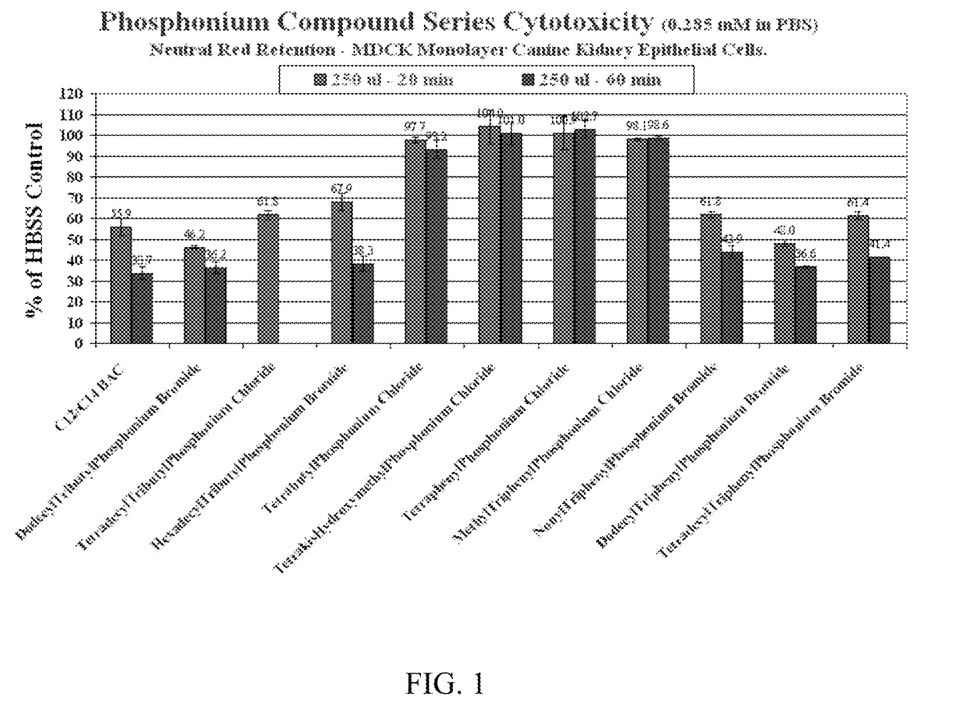
FIGS. 1 and 2 illustrate the relative cytotoxicity of compounds, some of which are in accordance with the present invention.
Figure 2:
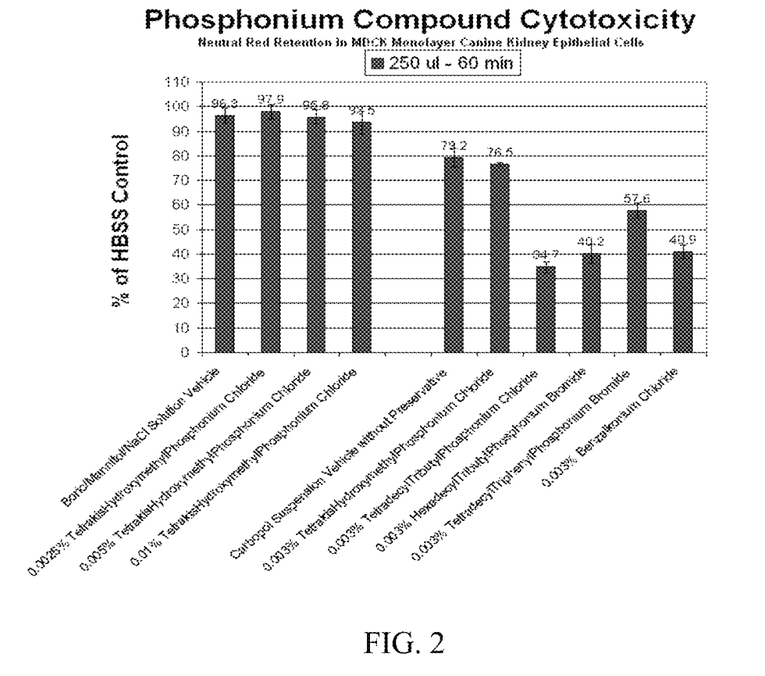

FIGS. 1 and 2 illustrate the cytotoxicity of the compounds shown in the above examples. In particular, these Figures show the neutral red retention of canine epithelial cells for the various compounds with the greater neutral red retention showing the lower the cytotoxicity. As can be seen in FIG. 1, many phosphonium compounds that exhibit substantially equivalent antimicrobial efficacy relative to BAC also exhibit similar or substantially lower levels of cytotoxicity relative to BAC. As such, many of these phosphonium antimicrobial agents can be used as suitable replacements for benzalkonium chloride particularly in circumstances where benzalkonium chloride is unsuitable (e.g., is incompatible with other ingredients in a solution). Notably, tetrakishydroxymethylphosphonium chloride exhibited an extremely low level of cytotoxicity, while, as shown above, it exhibits highly desirable antimicrobial efficacy. Moreover, with reference to FIG. 2, it can be seen that tetrakishydroxymethylphosphonium chloride exhibits extremely low toxicity regardless of concentration and/or the vehicle into which it is placed.

We claim:
1. A pharmaceutical composition, comprising:
an phosphonium antimicrobial agent according to the following formula:

wherein:
$R_1$, $R_2$, $R_3$ and $R_4$ are selected from one or more hydroxyalkyl groups and the one or more hydroxyl alkyl groups are selected from hydroxylmethyl, hydroxyethyl and hydroxypropyl; and
$X^-$ is a counterion and a halogen; and
water;
wherein the phosphonium antimicrobial agent is at least 0.0001 w/w % of the composition and is no greater than 0.5 w/w %; and
wherein the composition is a contact lens disinfecting solution or an ophthalmic pharmaceutical solution and the composition is sterile within a container.

2. A pharmaceutical composition as in claim 1 wherein the phosphonium antimicrobial agent is tetrakishydroxymethyl phosphonium chloride.

3. A pharmaceutical composition as in claim 2 wherein the composition is an ophthalmic composition disposed within an eye dropper.

4. A pharmaceutical composition as in claim 2 wherein the composition is a contact lens disinfecting solution or an ophthalmic pharmaceutical solution and the composition is sterile within the container.

5. A pharmaceutical composition as in claim 4, wherein the container is a dispenser contains at least 0.5 ml, but no greater than 1000 ml of the composition.

6. A pharmaceutical composition as in claim 5 wherein the composition has a pH at least 6 but no greater than 8.

7. A pharmaceutical composition as in claim 6 wherein the composition has an osmolality of at least 240 but no greater than 360.

* * * * *